US009375335B2

(12) United States Patent
Bialas et al.

(10) Patent No.: US 9,375,335 B2
(45) Date of Patent: Jun. 28, 2016

(54) CATHETER HAVING HYDRAULIC ACTUATOR

(71) Applicant: ABBOTT CARDIOVASCULAR SYSTEMS INC., Santa Clara, CA (US)

(72) Inventors: Michael Bialas, Wildomar, CA (US); John E. Papp, Temecula, CA (US); John Simpson, Carlsbad, CA (US); Wouter Erik Roorda, Palo Alto, CA (US); Matt Gillick, Murrieta, CA (US); Michael L. Green, Pleasanton, CA (US); David P. Strauss, Temecula, CA (US); Duane M. DeMore, Temecula, CA (US); Robert P. Barbier, Perris, CA (US); Marc Gianotti, Wiesendangen (CH)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/643,110

(22) Filed: Mar. 10, 2015

(65) Prior Publication Data
US 2015/0245937 A1 Sep. 3, 2015

Related U.S. Application Data

(63) Continuation of application No. 13/467,660, filed on May 9, 2012, now Pat. No. 9,011,513.

(51) Int. Cl.
*A61F 2/966* (2013.01)

(52) U.S. Cl.
CPC ..................................... *A61F 2/966* (2013.01)

(58) Field of Classification Search
CPC ............ A61F 2/699; A61F 2/95; A61F 2/958; A61F 2/2436
USPC ............................................ 604/284; 606/108
See application file for complete search history.

(56) References Cited

U.S. PATENT DOCUMENTS

| 5,695,468 | A | * | 12/1997 | Lafontaine et al. | ......... 604/96.01 |
| 5,709,703 | A | * | 1/1998 | Lukic et al. | .................. 623/1.12 |
| 5,776,141 | A | | 7/1998 | Klein et al. | |
| 5,817,101 | A | | 10/1998 | Fiedler | |
| 6,056,759 | A | | 5/2000 | Fiedler | |
| 6,113,608 | A | * | 9/2000 | Monroe et al. | ............... 623/1.11 |

(Continued)

OTHER PUBLICATIONS

U.S. Appl. No. 14/653582, filed Jun. 18, 2015.

(Continued)

*Primary Examiner* — Julie A Szpira
(74) *Attorney, Agent, or Firm* — Baker Botts L.L.P.

(57) ABSTRACT

Catheter for delivery of a medical device such as a stent or filter includes an inner tubular member and an outer tubular member movable relative to the inner tubular member. The outer tubular member is disposed at the distal end of the inner tubular member. The inner tubular member includes a fluid lumen defined therein, the fluid lumen having a fluid flow port directed to the exterior surface of the inner tubular member. A pressure chamber is defined by the inner tubular member, the outer tubular member, a proximal seal and a distal seal, and is in fluid communication with the fluid flow port, wherein fluid introduced through the fluid flow port and into the pressure chamber applies a force on the proximal seal to move the outer tubular member in a proximal direction allowing the medical device constrained by the outer tubular member to be released.

26 Claims, 12 Drawing Sheets

(56) References Cited

U.S. PATENT DOCUMENTS

| | | | |
|---|---|---|---|
| 6,214,037 B1* | 4/2001 | Mitchell et al. | 623/1.11 |
| 6,287,285 B1 | 9/2001 | Michal et al. | |
| 6,425,898 B1 | 7/2002 | Wilson et al. | |
| 6,541,116 B2 | 4/2003 | Michal et al. | |
| 6,605,109 B2* | 8/2003 | Fiedler | 623/1.12 |
| 6,884,257 B1 | 4/2005 | Cox | |
| 6,945,989 B1 | 9/2005 | Betelia et al. | |
| 7,740,652 B2 | 6/2010 | Gerdts et al. | |
| 7,799,065 B2* | 9/2010 | Pappas | 623/1.11 |
| 8,435,279 B2* | 5/2013 | Beyerlein et al. | 623/1.11 |
| 8,685,076 B2 | 4/2014 | Gerdts et al. | |
| 9,011,513 B2 | 4/2015 | Bialas et al. | |
| 2002/0009535 A1 | 1/2002 | Michal et al. | |
| 2002/0045929 A1* | 4/2002 | Diaz | 623/1.11 |
| 2002/0058951 A1* | 5/2002 | Fiedler | 606/108 |
| 2004/0193243 A1 | 9/2004 | Mangiardi et al. | |
| 2007/0078506 A1 | 4/2007 | McCormick et al. | |
| 2007/0123971 A1 | 5/2007 | Kennedy et al. | |
| 2009/0018529 A1 | 1/2009 | Hoffman et al. | |
| 2009/0312832 A1* | 12/2009 | Delap | 623/1.11 |
| 2011/0307049 A1 | 12/2011 | Kao | |
| 2013/0073024 A1 | 3/2013 | Russo et al. | |
| 2013/0297011 A1 | 11/2013 | Morris et al. | |
| 2013/0304180 A1 | 11/2013 | Green et al. | |
| 2013/0304181 A1 | 11/2013 | Green et al. | |
| 2014/0214151 A1 | 7/2014 | Ibeling | |
| 2014/0276412 A1 | 9/2014 | Shumer et al. | |
| 2014/0277356 A1 | 9/2014 | Shumer et al. | |

OTHER PUBLICATIONS

U.S. Appl. No. 13/467,660, Oct. 7, 2013 Non-Final Office Action.
U.S. Appl. No. 13/467,660, Jan. 7, 2014 Response to Non-Final Office Action.
U.S. Appl. No. 13/467,660, Jul. 17, 2014 Final Office Action.
U.S. Appl. No. 13/467,660, Oct. 14, 2014 Response to Final Office Action.
U.S. Appl. No. 13/467,660, Nov. 25, 2014 Notice of Allowance.
U.S. Appl. No. 13/467,660, Feb. 25, 2015 Issue Fee Payment.
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
International Search Report for PCT/US2013/068306, dated Jan. 8, 2014.
International Search Report for PCT/US2013/030830, dated Jan. 15, 2014.
International Search Report and Written Opinion for PCT/US2013/069477, dated Jan. 8, 2014.
U.S. Appl. No. 13/797,636, Oct. 30, 2015 Response to Non-Final Office Action.
U.S. Appl. No. 13/801,588, Aug. 20, 2015 Non-Final Office Action.

* cited by examiner

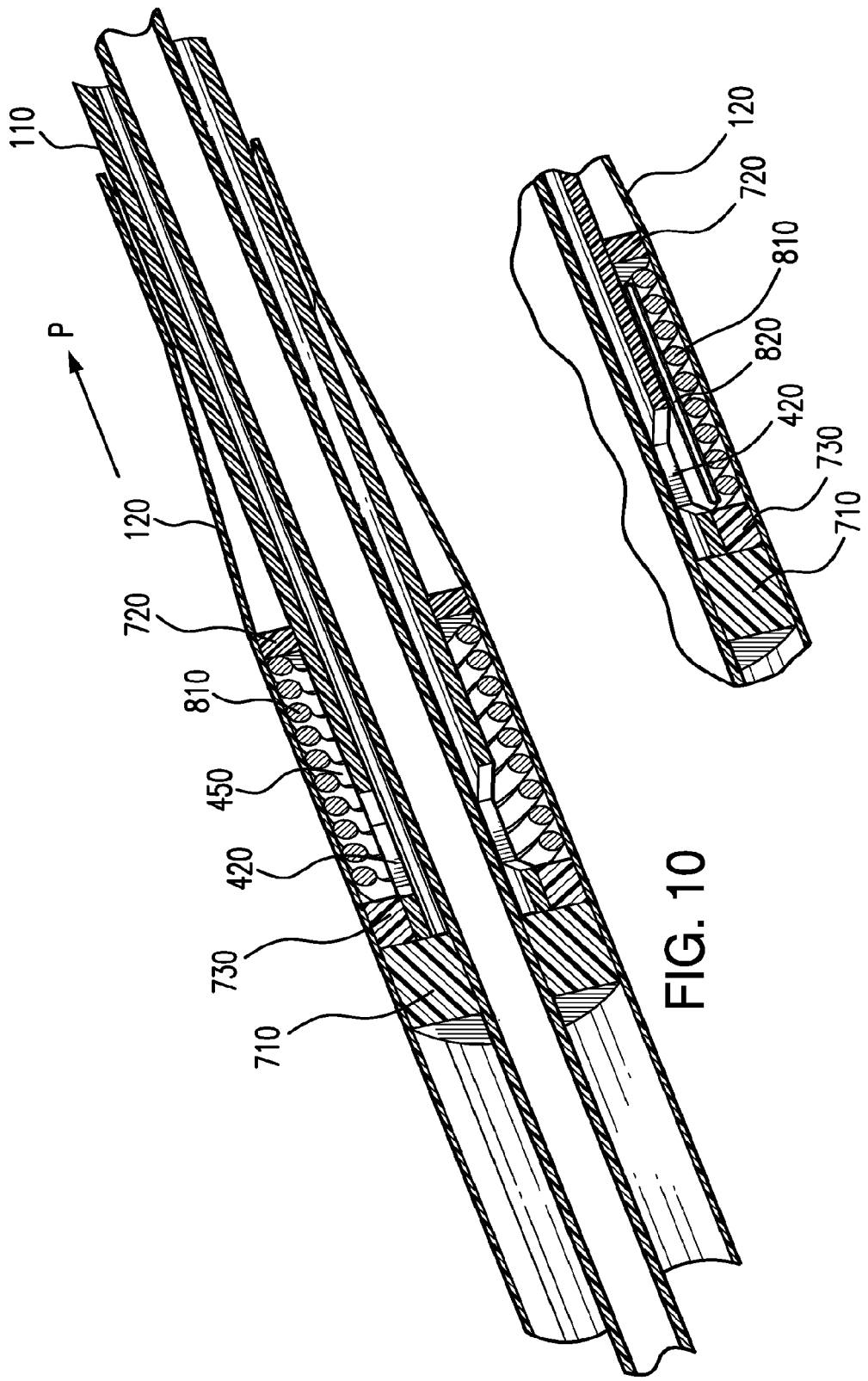

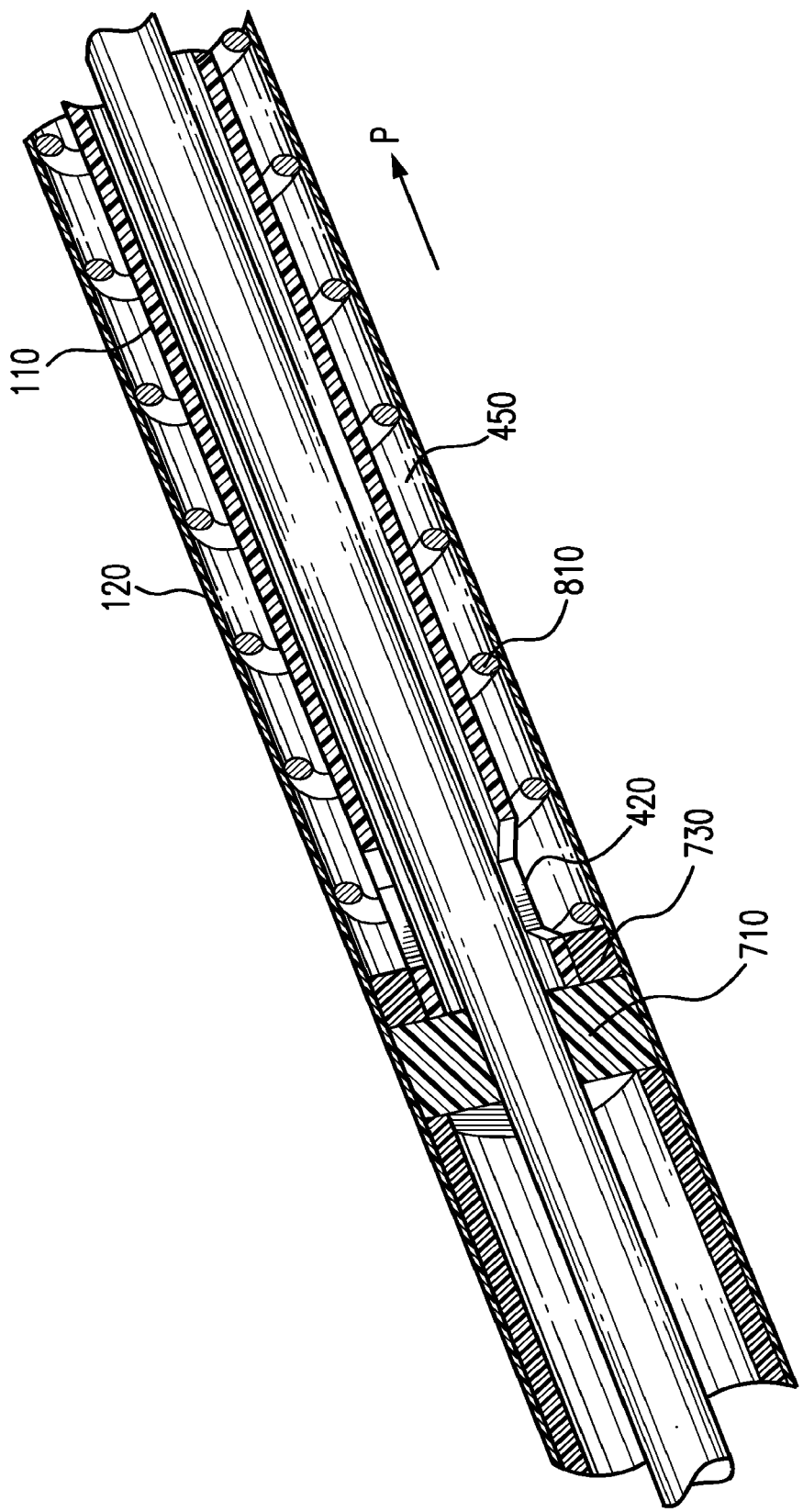

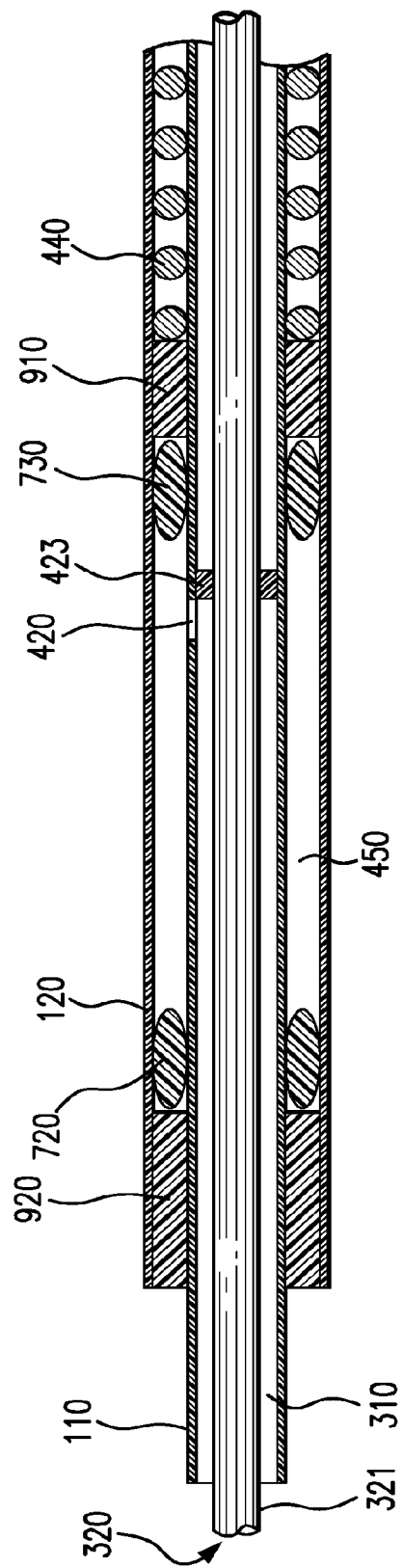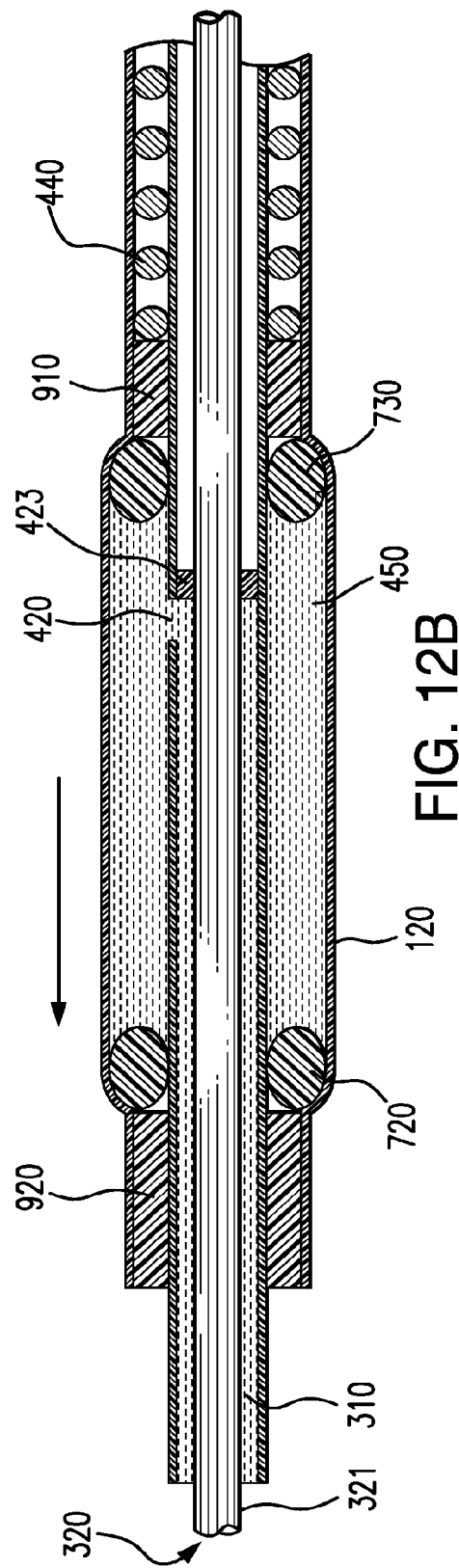

CATHETER HAVING HYDRAULIC ACTUATOR

CROSS REFERENCE TO RELATED APPLICATIONS

This application is a continuation of and claims priority to U.S. application Ser. No. 13/467,660 filed on May 9, 2012, the content of which is hereby incorporated by reference in its entirety.

BACKGROUND OF THE DISCLOSED SUBJECT MATTER

1. Field of the Disclosed Subject Matter

The disclosed subject matter relates to catheters used in the delivery of medical devices such as self-expanding stents for treating the luminal systems of a patient. Specifically, the disclosed subject matter relates to a delivery catheter having a retractable sheath moved by a hydraulic actuator.

2. Description of the Related Art

A variety of systems using a retractable sheath are known for intraluminal delivery of a medical device, such as a stent or filter. However, there remains a need for continued improvement of such known delivery systems.

An example of such a system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional self-expanding stent delivery systems generally comprise a handle portion and an elongated shaft, wherein the stent is disposed within a delivery portion at the distal end of the shaft. To deploy the stent, an outer sheath is provided which can be retracted relative to the stent to release the stent from its delivery configuration. The sheath in such systems generally spans the full length of the catheter resulting in an increased profile and stiffness over the entire length of the catheter. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Because the stent may embed in the outer sheath during storage and shipping, and due to larger static friction forces, a large amount of initial input is typically required to release the stent which may lead to incorrect placement. When initially releasing the stent, it may be desirable to slowly pull back the sheath for proper placement and then more readily retract the sheath to prevent inadvertent movement of the stent.

Further, the amount of force that is required to retract the sheath, particularly for stents of greater length as required for peripheral indications, can be substantial. Therefore there is a need for an improved delivery system for self-expanding stents having reduced force requirements for delivery of a self-expanding stent.

There thus remains a continued need for an efficient and economic system for delivering a medical device that is easy to use and provides accurate placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a hydraulic delivery system for a medical device such as a self-expanding stent or the like. The delivery system includes a catheter having an inner tubular member having a proximal end portion, a distal end portion and an exterior surface. The inner tubular member has a fluid lumen defined therein. The fluid lumen has a fluid flow port defined by the exterior surface along the distal end portion of the inner tubular member. The catheter further has an outer tubular member movable relative to the inner tubular member, the outer tubular member having a proximal end, a distal end an interior surface directed toward the exterior surface of the inner tubular member. The catheter has a proximal seal extending from the interior surface of the outer tubular member toward the exterior surface of the inner tubular member, the proximal seal located proximal to the fluid flow port.

The catheter also has a distal seal extending from the exterior surface of the inner tubular member toward the interior surface of the outer tubular member, the distal seal located distal to the fluid flow port. A pressure chamber is defined by the proximal seal, the distal seal, the exterior surface of the inner tubular member and the interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction.

In one embodiment the inner tubular member includes a guidewire lumen. The fluid lumen can be configured to receive a guidewire and further include proximal and distal guidewire seals to seal around a guidewire disposed therethrough. Alternatively, the guidewire lumen can be defined by a guidewire tube disposed within the fluid lumen. The catheter can also include a marker secured to the inner tubular member to seal a distal end of the fluid lumen distal of the fluid flow port. The marker can have an opening therein to allow a guidewire to pass therethrough.

As embodied herein, the proximal seal and the distal seal can be formed of hydrophilic material. Alternatively, the proximal seal and the distal seal can be formed of hydrophobic material. Further the proximal and distal seals can be expandable or made of a low durometer rubber having a compressed condition and an expanded condition.

In accordance with another aspect of the disclosed subject matter, the catheter includes a bellows component attached to the exterior surface of the inner tubular member and in fluid communication with the fluid flow port, wherein fluid introduced through the fluid flow port expands the bellows component to retract the outer tubular member.

In accordance with yet another aspect of the disclosed subject matter, the catheter includes a spring disposed to bias the outer tubular member in the proximal direction. The spring can be formed of any suitable material such as metal or metal alloy. The spring can have a constant pitch or a varied pitch, and a constant diameter or a varied diameter. Further, a dissolvable adhesive can be applied to maintain the spring in a compressed configuration until the adhesive is dissolved. Alternatively, a releasable clip can be attached to the spring to temporarily secure the spring in a compressed configuration, or an inflatable balloon can be used to retain the spring in a compressed configuration when the inflatable balloon is inflated. The inflatable balloon can have a balloon port, the balloon being moveable to align the balloon port with the fluid flow port for deflation of the balloon. Furthermore, in another embodiment of the disclosed subject matter, as the spring is axially compressed, the spring expands radially to lock against the interior surface of the outer tubular member. The outer tubular member is configured to expand radially under high pressure, such that the interference between the outer tubular member and spring is relieved to allow the spring to expand axially to assist in the retraction of the outer tubular member.

Alternatively, the outer tubular member can be formed of a shape memory material wherein the outer tubular member is radially expandable upon increased fluid temperature in the pressure chamber.

In accordance with another aspect of the disclosed subject matter, the outer tubular member comprises a multilayer tube having a flexible inner layer and a rigid outer layer. Alternatively, the outer tubular member can have a rigid inner layer and a flexible outer layer wherein the rigid inner layer is formed of a dissolvable material.

In another embodiment, the outer tubular member is formed of a bi-stable material having a contracted configuration and an expanded configuration. The outer tubular member transitions from the contracted configuration to the expanded configuration upon increased fluid pressure in the pressure chamber.

A strengthening member can be disposed along a length of the inner tubular member corresponding to the pressure chamber. The catheter includes a stent and stent seat disposed at the distal end of the inner tubular member.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 6A is a cross sectional view of the catheter of FIG. 6 taken at line 6A.

FIG. 10 is a cross sectional perspective view of the catheter of FIG. 9 and FIG. 10A is a detail of the cross sectional perspective view of FIG. 10 further having a membrane.

FIG. 11 is a cross sectional side view of the catheter of FIG. 10 with the sheath in a retracted position.

FIGS. 12A-12B are schematic cross sectional side views of an embodiment of the distal end of a catheter in accordance with the disclosed subject matter.

DETAILED DESCRIPTION

Reference will now be made in detail to embodiments of the disclosed subject matter, an example of which is illustrated in the accompanying drawings. The disclosed subject matter will be described in conjunction with the detailed description of the system.

As disclosed herein, the devices presented herein can be used for treating the luminal system of a patient. In particular, the disclosed subject matter is particularly suited for treatment of the cardiovascular system of a patient, such as delivery of a medical device into the vasculature.

In accordance with the disclosed subject matter, a hydraulic delivery system for a medical device, such as a self-expanding stent or the like is provided. The delivery system includes a catheter having an inner tubular member having a proximal end portion, a distal end portion and an exterior surface. The inner tubular member has a fluid lumen defined therein. The fluid lumen has a fluid flow port defined by the exterior surface along the distal end portion of the inner tubular member. The catheter further has an outer tubular member movable relative to the inner tubular member, the outer tubular member having a proximal end, a distal end an interior surface directed toward the exterior surface of the inner tubular member. The catheter has a proximal seal extending from the interior surface of the outer tubular member toward the exterior surface of the inner tubular member, the proximal seal located proximal to the fluid flow port. The catheter also has a distal seal extending from the exterior surface of the inner tubular member toward the interior surface of the outer tubular member, the distal seal located distal to the fluid flow port. A pressure chamber is defined by the proximal seal, the distal seal, the exterior surface of the inner tubular member and the interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction.

Figure 1:
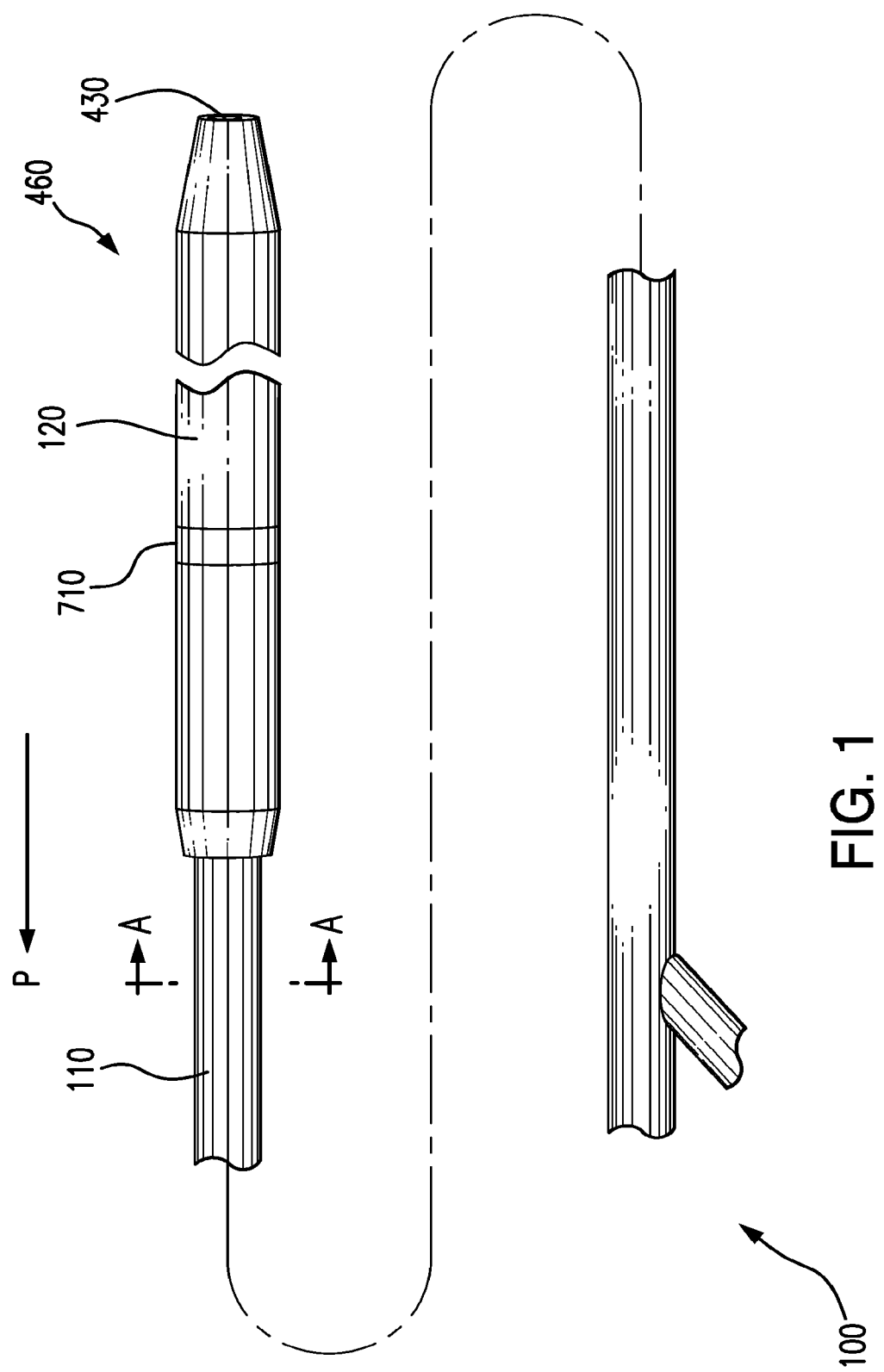
FIG. 1 is a schematic side view of a representative catheter in accordance with the disclosed subject matter.
Figure 2:
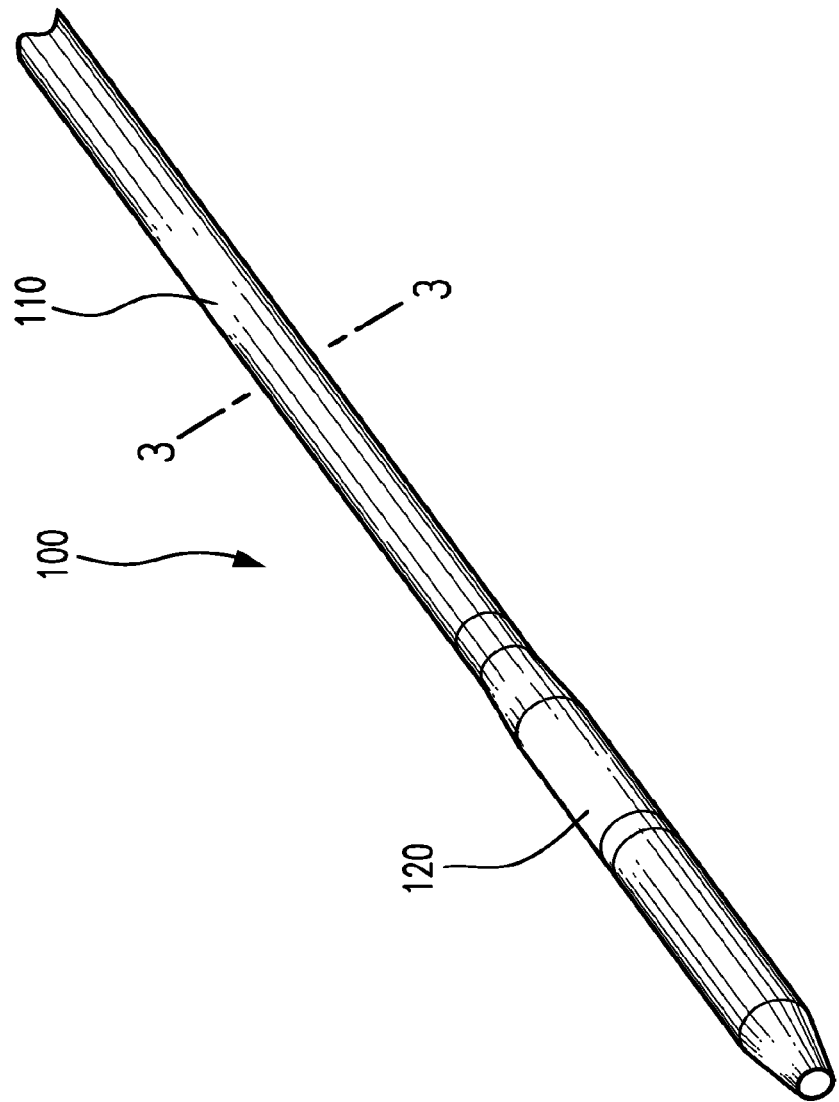
FIG. 2 is a perspective view of the distal end section of the catheter of FIG. 1.

Solely for purpose of illustration, an exemplary embodiment of a hydraulic delivery system for a self-expanding stent or the like, at least a portion of which is delivered within a vasculature, is shown schematically in FIGS. 1 and 2. The examples herein are not intended to limit the scope of the disclosed subject matter in any manner. Particularly, and as illustrated, the hydraulic delivery system embodied herein is a catheter 100, which includes an inner tubular member 110 having a proximal end portion, a distal end portion, and an exterior surface. The catheter 100 further includes an outer tubular member or sheath 120 which is movable relative to the inner tubular member 110 and has a proximal end, a distal end and an interior surface directed toward the exterior surface of the inner tubular member 110. As shown in FIG. 2, the sheath is disposed only at a distal end portion of the catheter. As described further herein, the catheter of the disclosed subject matter can be configured to deliver a medical device, such as a stent, of any suitable length. That is, the catheter can be configured to generate a force sufficient to retract the outer tubular member, wherein the generated force is greater than the resistance force caused by the medical device acting on the outer tubular member.

Figure 3:
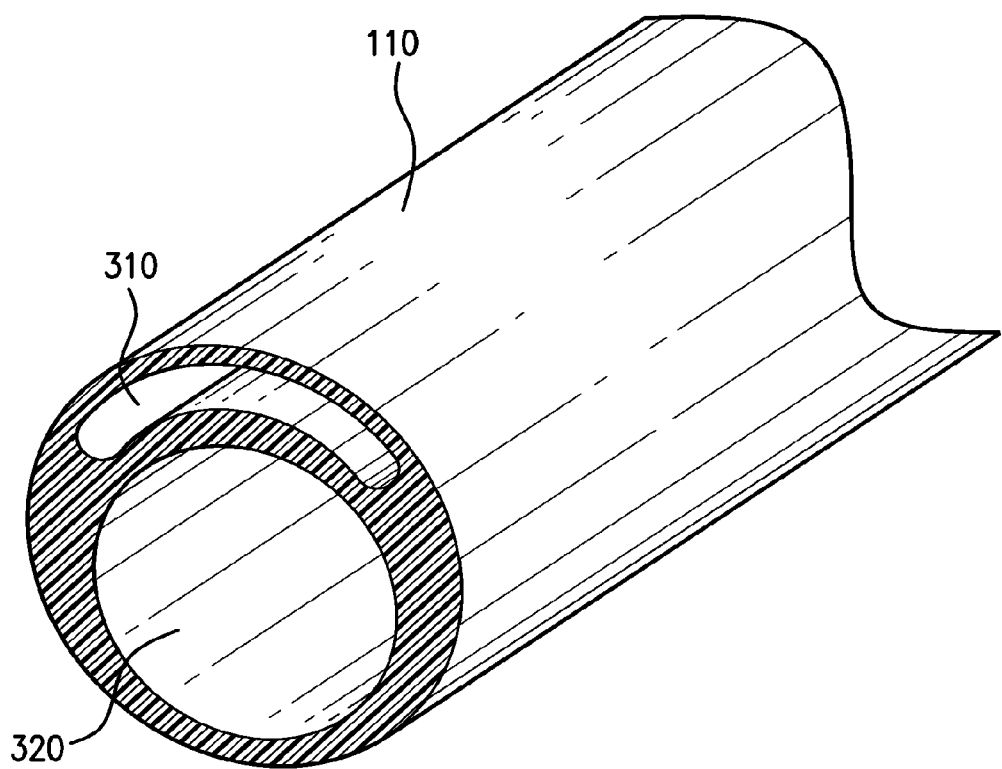
FIG. 3 is a cross sectional perspective view of the catheter of FIG. 2 taken along line 3-3.

Solely for purpose of illustration, reference is made to FIG. 3 which depicts a representative cross sectional view of an exemplary inner tubular member 110 along lines 3-3 of FIG. 2, in accordance with the disclosed subject matter. The inner tubular member 110 further has a fluid lumen 310 defined therein. In one embodiment the inner tubular member can also have a guidewire lumen 320 defined at least along a length therein. For example, the guidewire lumen 320, if provided, can extend over the entire length of the inner tubular member 110 such as for an "over-the-wire" configuration, or only along a distal length such as for a "rapid exchange" embodiment. Alternatively the catheter 100 can have a single-lumen design and the guidewire and pressurized fluid can share the same lumen (not shown), wherein a seal or valve can be provided at distal and proximal ends.

In another embodiment, as shown in FIGS. 12A and 12B solely for purposes of illustration, the guidewire lumen 320 can be defined at least in part by a separate guidewire tube 321 disposed within a fluid lumen 310 and sealed at either side, such as for example, by a marker 423 (note: only distal seal shown). Such coaxial configurations allow for reduced diameter of the inner tubular member 110, and thus reduced profile. Indeed the guidewire tube 321 defining the guidewire lumen 320 can be formed by a thin membrane of suitable strength to prevent the guidewire from penetrating therethrough. Hydraulic fluid can thus flow within the fluid lumen 310 but outside the guidewire lumen 320.

Figure 4:
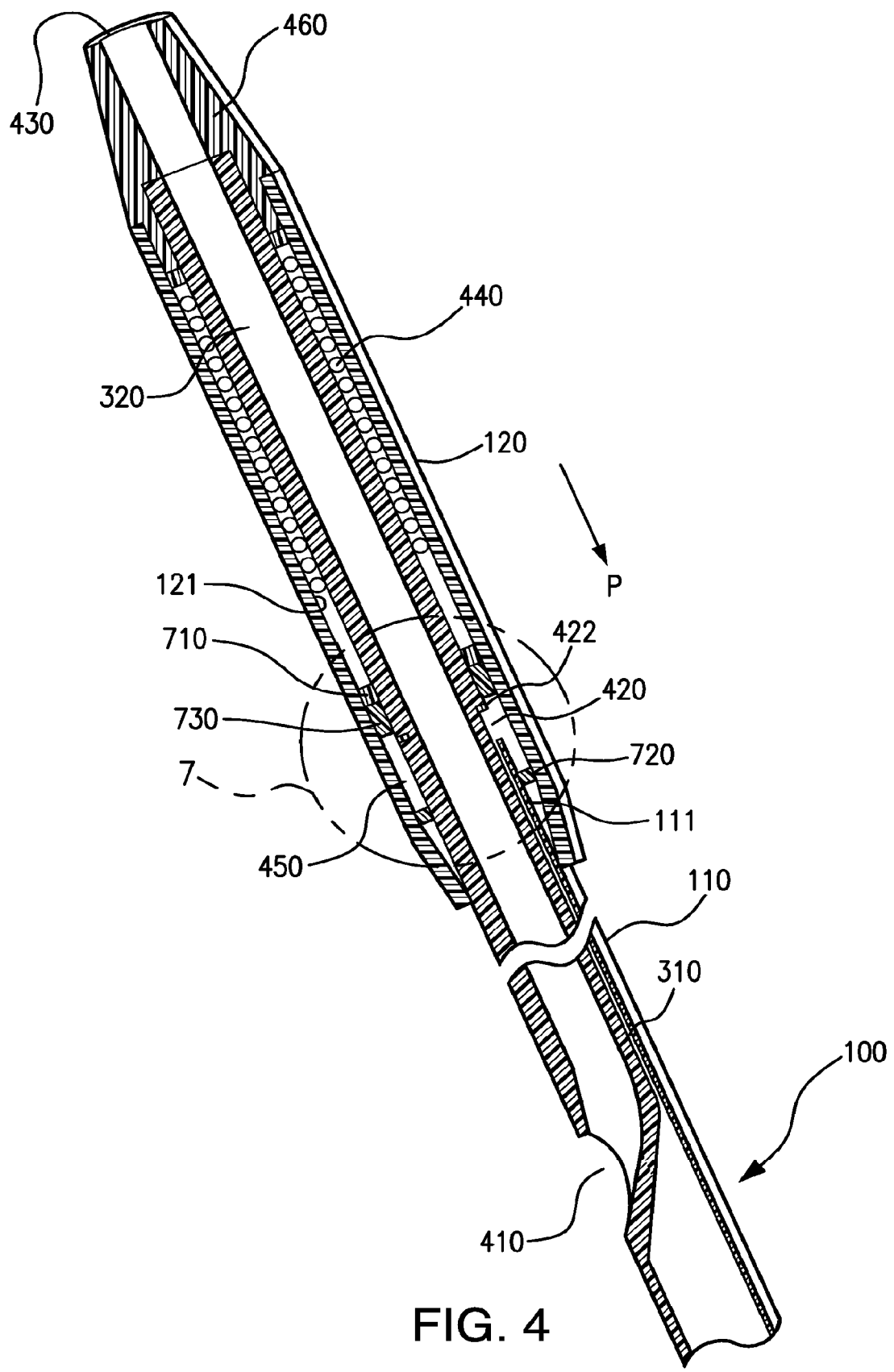
FIG. 4 is a cross sectional perspective view of the distal end section of a catheter in accordance with the disclosed subject matter with the sheath in a closed position.

Solely for purpose of illustration, reference is now made to a rapid exchange configuration of the catheter disclosed herein as shown in FIG. 4. Generally, the catheter includes an inner tubular member 110 having a proximal end portion, a distal end portion and an exterior surface. The inner tubular member 110 further includes a fluid lumen 310 having a fluid flow port 420 defined by the exterior surface 111 along a distal end portion of inner tubular member 110. The catheter further includes an outer tubular member 120 movable relative to the inner tubular member 110 and having a proximal end, a distal end and an interior surface 121 directed toward the exterior surface 111 of the inner tubular member 110. As embodied herein, the rapid exchange catheter further includes guidewire lumen 320 extending along a distal end portion of the catheter and including a proximal guidewire port 410, a distal guidewire port 430.

Figure 5:
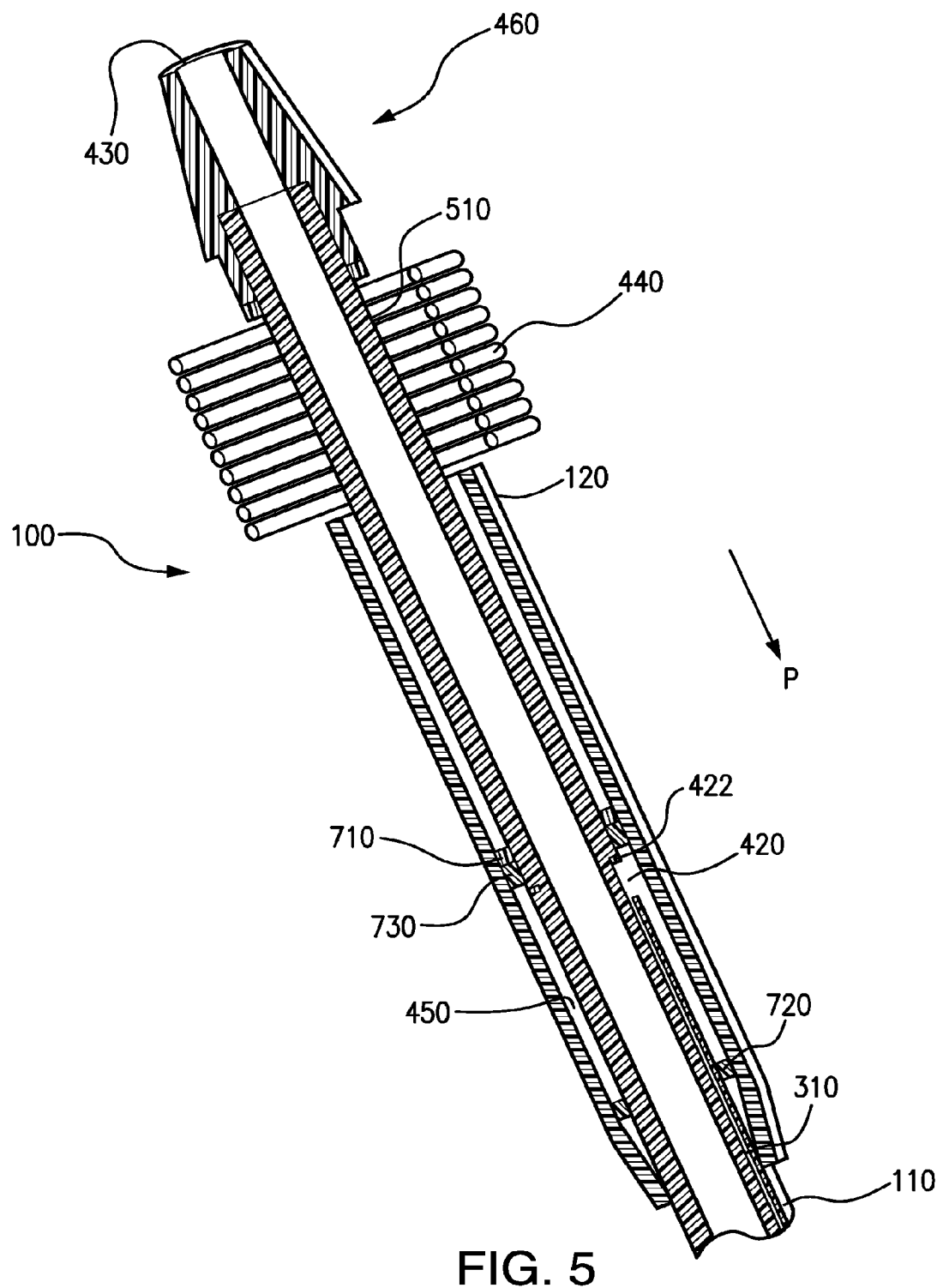
FIG. 5 is a cross sectional side view of the distal end of the catheter of FIG. 4 with the sheath in a fully retracted position.
Figure 6:
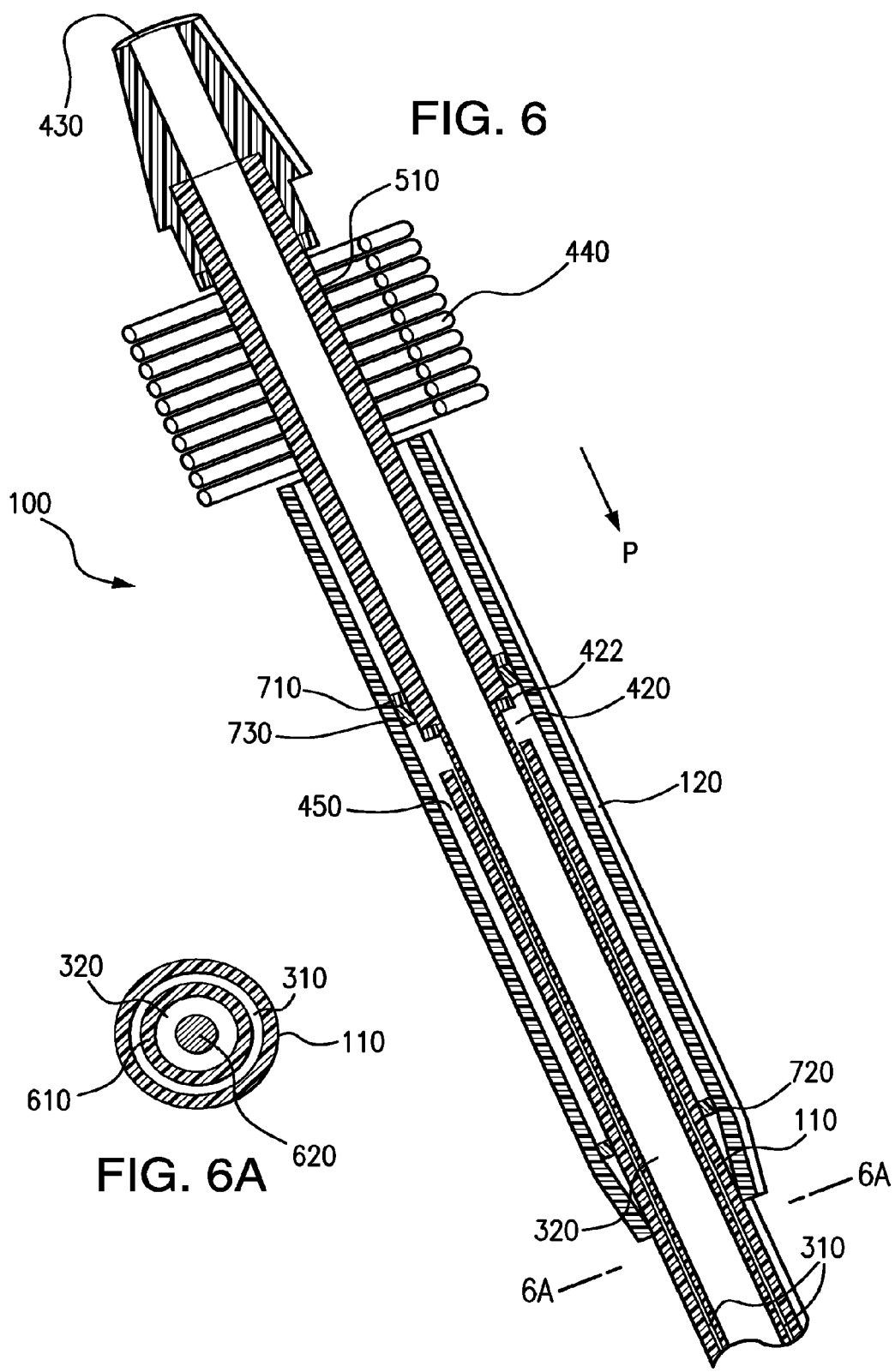
FIG. 6 is a cross sectional side view of the distal end section of an alternative catheter in accordance with the disclosed subject matter with the sheath in a fully retracted position.

As illustrated, the outer tubular member 120 can be moved from an extended position as shown in FIG. 4 to a retracted position shown in FIG. 5. When extended, the outer tubular member 120 retains a medical device, such as a stent 440 as depicted herein, in a compressed or delivery condition. A distal tip 460 can also be provided to further enclose the medical device during delivery. When the outer tubular member 120 is retracted (as shown in FIGS. 5 and 6), the medical device is unsheathed and allowed to expand to a deployed condition.

The fluid lumen 310 has a fluid flow port 420. The fluid flow port 420 is defined with the exterior surface of the inner tubular member 110 along the distal end portion of inner tubular member 110. As described in more detail below, the fluid flow port 420 allows fluid to pass from within fluid lumen 310 into the space defined by the inner tubular member 110 and outer tubular member 120 and between seals 720 and 730. A marker 422 can define the distal end of the fluid flow port 420.

Figure 7:
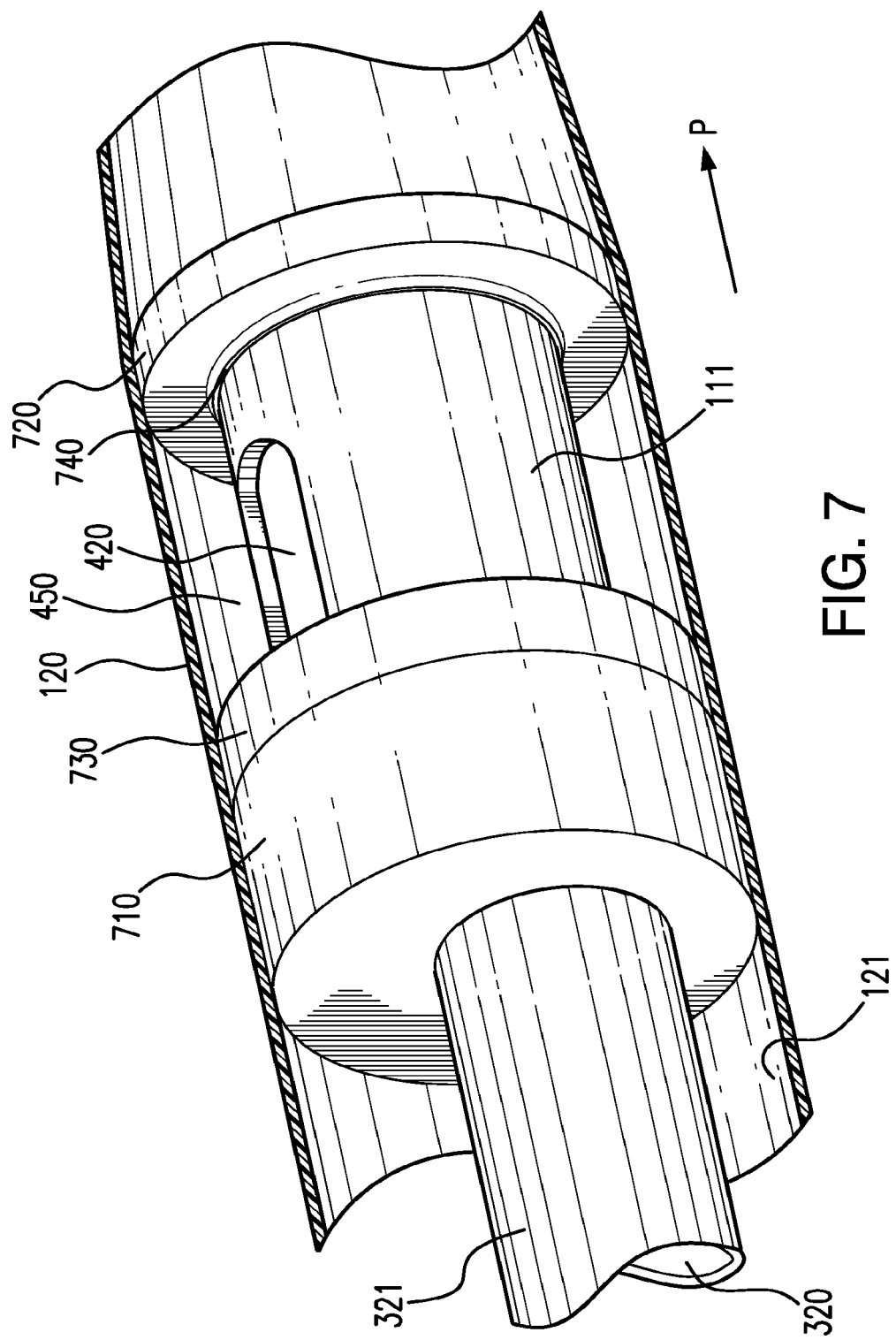
FIG. 7 is a detail perspective view of the catheter of FIG. 4 along line 7-7.
Figure 8:
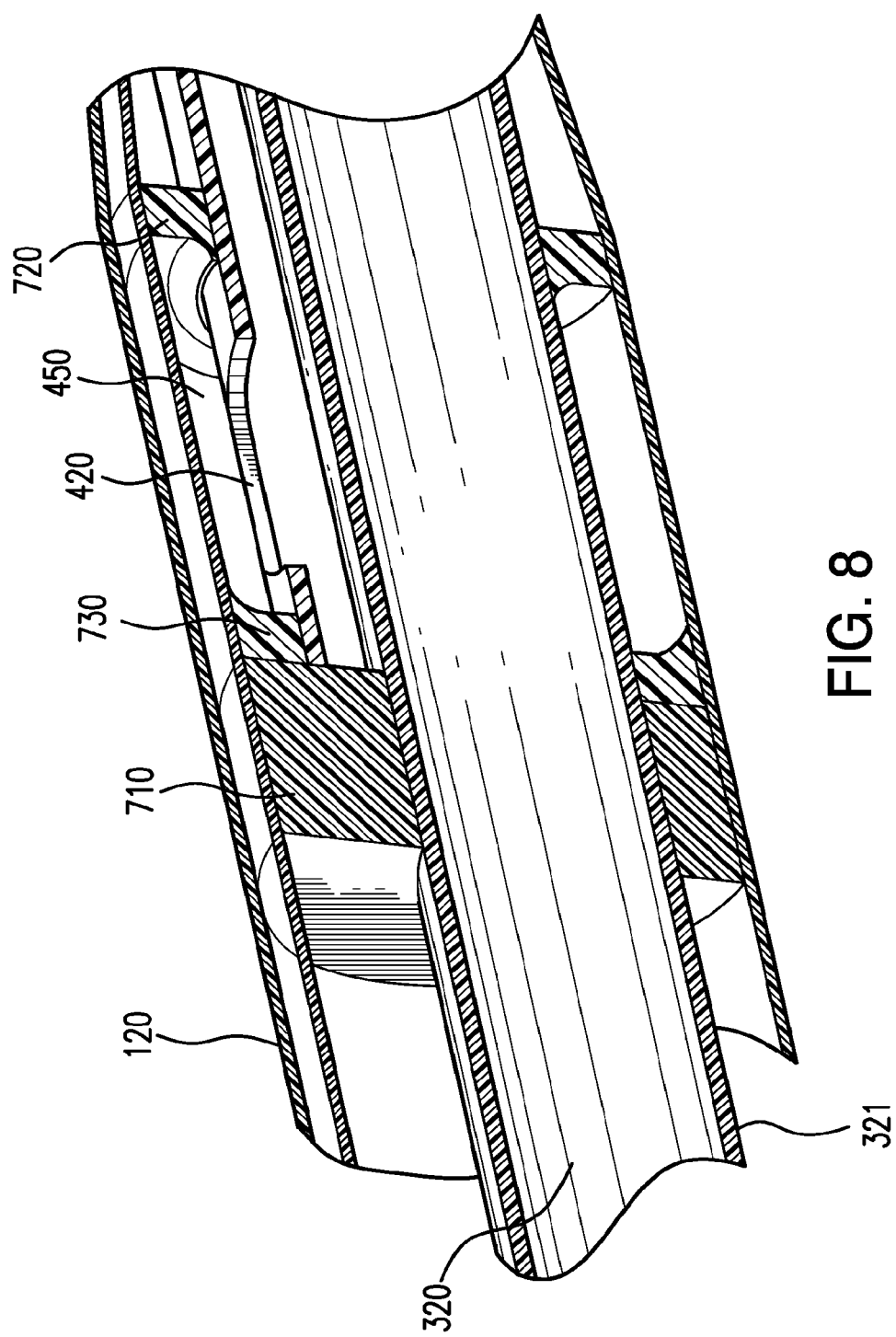
FIG. 8 is a cross sectional perspective view of the catheter of FIG. 7.

As shown in FIGS. 7 and 8, solely for purpose of illustration, the catheter further includes a proximal seal 720. The proximal seal 720 extends from the interior surface of the outer tubular member 120 toward the exterior surface of the inner tubular member 110 and is located proximal to fluid flow port 420. The proximal seal 720 is fixed to the interior surface of the outer tubular member 120 and moves freely relative to the inner tubular member 110.

With continued reference to FIGS. 7 and 8, catheter 100 also includes a distal seal 730. The distal seal 730 extends from the exterior surface of the inner tubular member 110 toward the interior surface of the outer tubular member 120 and is located distal to fluid flow port 420. The distal seal 730 is fixed to the exterior surface of the inner tubular member 110 and moves freely relative to the interior surface of the outer tubular member 120. In this manner, the outer tubular member 120 moves freely relative to the distal seal 730. As embodied herein, and as shown in FIG. 7, one or both of the proximal and distal seal can form a wiper seal 740 across the corresponding surface.

As shown in FIGS. 7 and 8, solely for purpose of illustration, the catheter 100 further has pressure chamber 450 therein defined by the proximal seal 720, distal seal 730, the exterior surface 111 of the inner tubular member 110, and the interior surface 121 of the outer tubular member 120. Pressure chamber 450 is in fluid communication with fluid flow port 420.

As recognized in the art, the outer tubular member 120 constrains the medical device to be delivered. The medical device, e.g., a self expanding stent, is deployed by retracting the outer tubular member 120 (catheter sheath). Retraction is achieved by the introduction of fluid under pressure through the fluid lumen 310 using a conventional device, such as an indeflator or a syringe. The indeflator can include a threaded engagement or other locking mechanism to control pressurization and depressurization of the pressure chamber (not shown). Additionally, a pressure gauge can be provided with the indeflator to monitor the pressure system of the catheter. The indeflator can be configured to allow for the rapid release of hydraulic pressure to stop or inhibit the deployment of the stent. The indeflator can also be configured to create and/or maintain negative pressure in the catheter. The indeflator can further create a vacuum that decreases the profile of the catheter. For example, by creating a vacuum, the outer tubular member 120 disclosed herein can be configured to decrease in profile and/or lock in position. An example of a suitable indeflator is an Atrion indeflator Atrion Medical-55ATM.

An adapter can be provided at the proximal end of the catheter for access to the fluid lumen and can be configured for connecting to a fluid source (not shown). With reference to FIG. 7, fluid is introduced into the fluid lumen and exits the fluid lumen at flow port 420 and fills pressure chamber 450. Once sufficient fluid is introduced into the pressure chamber 450, a force is applied on the distal and proximal seals. Because the distal seal 730 is fixed relative to the inner member, only the proximal seal 720 and outer tubular member attached thereto is capable of movement relative to the inner member in the proximal direction P. Movement of the proximal seal 720 upon the application of force in the pressure chamber 450 moves the outer tubular member 120 in the proximal direction P along the inner tubular member thereby allowing the medical device to be deployed. Distal seal 730, as embodied herein, is configured as a wiper-seal with the interior surface of outer tubular member 120. The outer tubular member 120 thus moves relative to distal seal 730. Proximal seal 720 mounted to the interior surface of outer tubular member 120 is configured as a wiper-seal with the exterior surface 111 of inner tubular member 110. The proximal seal 720 is free to move relative to the inner tubular member 110.

Although shown as a single piece seal construction in FIGS. 7 and 8, each seal of the disclosed subject matter can be a multi-piece seal assembly, if desired. For example, the seal assembly can include a seal member and a bushing to provide a backing to the seal member, as known in the art. As depicted in FIGS. 12A and 12B, the seals 720 and 730 can further be supported by proximal and distal bushings 920 and 910, respectively. In accordance with an aspect of the disclosed subject matter, the bushings can be constructed of any suitable material, including, but not limited to, PEEK, Pebax, HDPE, LDPE, a mixture of HDPE and LDPE, a Nylon blend such as L75/L25, or the like. Furthermore, the bushings can comprise a metallic material, combination low density polyethelene, silicon, nitril, soft Pebax 30, or other blends of suitable material, and can be coated with a suitable material as known in the art, and can include a coating.

As relatively high fluid pressures are needed to retract outer tubular member 120, the pressure chamber is formed to withstand such pressures with minimal to no leaks. A variety of suitable seal constructions and materials can be used, such as, but not limited to, sliding seals, rings, cups seals, lips seals, and compressed bushings. For example, each seal can be formed as a separate member and attached to the corresponding tube member, or can be formed as part of the tubular member. Solely for purposes of illustration, a hydrophilic material, such as, but not limited to, HydroMed™, Hydrothane™, Hydak®, can be used for the seals. Seals made of such material can be configured to swell when exposed to an aqueous environment, thus sealing more tightly while maintaining lubricity. The seals thus can comprise an expandable material or composite of materials to increase accordingly to match the dimensions of the outer tubular member. That is, the seal can be configured to expand with the outer tubular member to maintain an adequate seal.

As the pressure chamber expands, the exposed surface area of the seal also increases, resulting in a proportional increase in retraction force at a given fluid pressure. Thus, an expanding pressure chamber provides for greater retraction force at a given pressure. Seals made of such material can be configured to swell when exposed to an aqueous environment, thus sealing more tightly while maintaining lubricity. Alternatively, the proximal and distal seals can be coated with a hydrophobic layer such as oil or wax or made of hydrophobic material such as a fluorocarbon or olefins like polypropylene to be used with a suitable pressurized fluid. Solely for example, silicone seals can be provided with a Hydromer 2314-172 coating. In another embodiment, O-rings can be used for the seal constructions comprised of silicone, buna, or other suitable elastomers. Furthermore, solely for purpose of example, the seal can include soft tubing such as a low durometer Pebax. Additionally or alternatively, a high viscosity hydraulic fluid can be used to inhibit leaks.

Embodiments of the disclosed subject matter allow the pressure chamber to operate with a variety of different suitable pressures. Solely for purpose of example, in one embodiment the pressure chamber can handle a positive pressure of up to 750 psi, and a negative pressure of approximately 14 psi.

In accordance with another aspect, catheter 100 further includes a bellows, or bladder component within the chamber to prevent leaks. The bellows or bladder component is attached to the exterior surface of the inner tubular member 110 and is in fluid communication with the fluid flow port 420, wherein fluid introduced through the fluid flow port 420 expands the bellows component to retract the outer tubular member.

In yet another aspect of the disclosed subject matter, spacer elements (not shown) can be provided within the pressure chamber. The spacer elements can prevent the outer tubular member, proximal seal and distal seal from being collapsed during delivery and storage of the catheter. The spacer elements can also reduce the amount of fluid needed to retract the outer tubular member. The spacer elements can be made of any of a variety of suitable shapes and materials, such as ring members having diameters corresponding to the inner and outer diameters of the inner and outer tubular members, respectively.

If desired, the distal seal can form a bumper or stop member for the medical device. Alternatively, in accordance with another aspect of the disclosed subject matter, the catheter can include a stop 710 secured to the inner tubular member 110, as depicted in FIGS. 7 and 8. The stop is disposed distal to the pressure chamber 450 and proximal to the medical device to be delivered, e.g., the stent. In this manner, the stop 710 seals the hydraulic fluid lumen 310 but allows the guidewire tube 321 and/or guidewire (not shown) to pass through. Stop 710 can be made of or include a radiopaque material to provide the physician performing the procedure with visibility as to placement of the catheter so that the medical device can accurately be positioned at the treatment site. The stop 710 is thus a radiopaque marker. For example, the marker can be a radiopaque metallic ring, or made of a tungsten loaded polymer for increased softness and flexibility. Other suitable markers known can be used.

Figure 9:
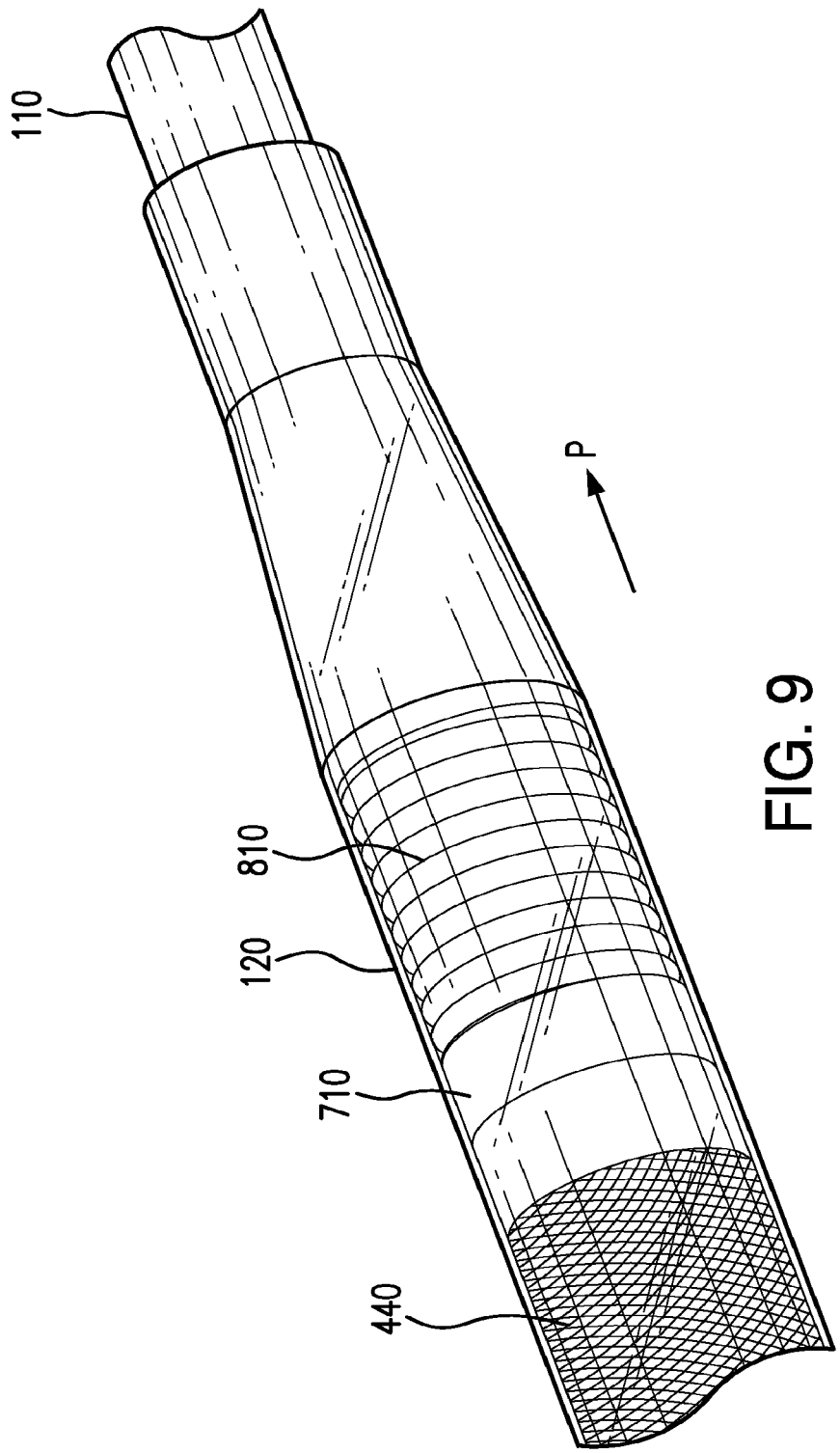
FIG. 9 is a detail perspective view of another embodiment of a catheter in accordance with the disclosed subject matter.

In accordance with another aspect of the disclosed subject matter and as depicted in FIGS. 9, 10 and 10A, a spring 810 can be provided to bias the outer tubular member 120 in the proximal direction P. For example, a greater amount of force may be needed to begin retracting the outer tubular member 120 due to static friction between the self-expanding stent 440 and the outer tubular member 120. Once the outer tubular member 120 begins retracting, significantly less force is required to complete the deployment. A coiled spring 810 can be used to provide an increase of force at the start of deployment.

FIGS. 9, 10, and 10A depict a side view and a cross sectional views, respectively, of an embodiment of the distal end section of a catheter employing a coiled spring 810, as described. The spring 810 is depicted in a compressed state with the outer tubular member 120 extended. As embodied herein in FIGS. 10 and 10A, solely for purposes of illustration, the spring 810 is disposed in the pressure chamber 450 between the proximal seal 720 and distal seal 730. In this manner, the spring 810 likewise can act as a spacer element, as previously described. Upon introduction of pressurized fluid into pressure chamber 450, the combination of force from the pressurized fluid and the spring 810 will cause outer tubular member 120 to begin to retract. As spring 810 expands, the force exerted on outer tubular member decreases. Thus a greater force is achieved at the beginning of deployment with a decreasing force as the spring expands. Solely for purposes of illustration, FIG. 11 shows a cross sectional view of the catheter of FIG. 10 with the outer tubular member 120 retracted and spring 810 in an expanded state.

As embodied herein, the friction of stent 440 against outer tubular member 120 is sufficient to prevent the spring 810 from expanding and the outer tubular member 120 from retracting prematurely. Additionally or alternatively, the spring 810 can be restrained and selectively released if desired. For example, the spring can be made of shape-memory material, such as nitinol. The nitinol spring is heat treated to have a first compressed length below a selected temperature and a second expanded length when heated above a selected temperature. The spring is then compressed and loaded into the pressure chamber and remains in the compressed state until heated above the selected temperature, e.g., body temperature or greater. Introducing a heated flushing solution through fluid port 420 causes the spring 810 to expand and deliver an initial force against fixed seal 730. The expansion of the spring assists the hydraulic system in overcoming static friction forces and possible embedding of the stent into the outer tubular member.

Additionally or alternatively the spring 810 can be secured in its compressed state by the use of a dissolvable adhesive. The adhesive can be dissolved by the introduction of a compatible flushing media through fluid port 420. In another embodiment, spring 810 can be held in its compressed state using a clip or the like (not shown) when loaded into the pressure chamber 450. In this case, a pullwire, filament or similar activation member can traverse the length of the catheter to deploy or release the clip and thus the spring. An end actuator on the pullwire can be provided coupled to the clip (not shown). After positioning the catheter at the treatment site the clip is removed by activating the pullwire, allowing the spring 810 to expand.

In accordance with another aspect of the disclosed subject matter, an inflatable balloon or membrane can be provided to secure the compressed spring in a compressed state. For example, and as depicted in FIG. 10A solely for purpose of illustration, the expandable balloon 820 or membrane can be located in the chamber 450 or within the guidewire lumen proximate the chamber to engage the spring when inflated. In this manner, the expandable balloon 820 or membrane is inflated prior to deployment to hold the compressed spring in the compressed state. The balloon 820 or membrane is deflated, such as by rupturing the membrane with a guidewire after positioning the catheter at the treatment site. Alternatively, the expandable balloon 820 or membrane can be movable between a first position to maintain an expanded state and a second position in alignment with a port or the like to deflate the expandable membrane. For example, the balloon or membrane can be provided with a port, such that upon rotation of the balloon or membrane, the port is aligned with the fluid port 420 of the inner tubular member for release of the inflation medium. In this manner, the balloon or membrane can be inflated with any suitable inflation medium including a liquid or a gas. Additionally, the inflation medium can be withdrawn using a vacuum through the hydraulic port prior to refraction of the outer tubular member.

In an alternative embodiment, premature expansion of the spring 810 can be prevented by sizing the spring to fit within pressure chamber 450 such that the spring expands radially into engagement with surfaces of the inner and outer tubular member when compressed, but free of engagement when the spring is expanded. Upon introduction of pressurized fluid into the pressure chamber, the outer tubular member will slightly expand, radially, thus freeing the spring from engagement with the inner and outer members and allowing the spring to expand axially to exert retraction force on the seal.

The spring 810 is a compression spring and can be formed of any suitable material and can have any suitable configuration. Solely for purposes of illustration, the spring 810 can be formed of metal or a metal alloy, such as stainless steel. The spring 810 can also be formed of a shape-memory material such as nitinol. Further, the spring can be of constant pitch or variable pitch to suit the force required. As shown in FIGS. 9-11, spring 810 has a generally uniform cylindrical shape, however, it is understood that the spring can have variable diameters to suit the particular application. The thickness and cross section of the spring, the number of coils and the flatness of the ends are all variables that can be modified to achieve the desired spring force.

Reference is now made to FIG. 6, solely for purposes of illustration, which depicts an over-the-wire variation of the disclosed subject matter. In this embodiment, catheter 100 includes inner tubular member 110, outer tubular member 120 (shown in a retracted position), a guidewire lumen 320, and fluid lumen 310 having fluid flow port 420. Catheter 100 further includes medical devices, such as stent 440 as shown in an expanded state, stent seat 510, and a distal guidewire port 430.

As shown in FIG. 6A, solely for the purpose of illustration, the inner tubular member 110 or elongated catheter shaft of the catheter can include first and second tubular members 110 and 610, respectively, in coaxial relationship with each other to define a central guidewire lumen 320 within the first tubular member 110 and an annular fluid lumen 310 located between the first and second tubular members 610 of the inner tubular member or shaft. The fluid lumen 310 can supply a hydraulic medium under positive pressure and can withdraw the hydraulic medium, i.e., provide negative pressure, from pressure chamber 450 as desired. The catheter is sized and configured for delivery within a corresponding body lumen for the intended indication, such as a vasculature for vascular intervention. The catheter includes a guidewire lumen for delivery over a guidewire 620 as shown in FIG. 6A. The portion of the inner tubular member extending distal of the chamber can be defined by an extension of the first tubular member 110, or an extension of the second tubular member 610, or by a separate tubular member as desired. Although a coaxial shaft and over-the-wire (OTW) catheter configuration is depicted in FIG. 6, those skilled in the art will recognize that other configurations and known materials of construction can be used without departing from the scope of the disclosed subject matter, for example, the rapid exchange and/or dual lumen configurations as previously described.

In accordance with another aspect of the disclosed subject matter, the pressure chamber can be configured to increase in cross section when pressurized, such that a greater force is generated on the end seals due to the increased surface area. Reference is now made to FIGS. 12A-12B, solely for purposes of illustration, which depict an exemplary embodiment of a cross section of another catheter configuration in accordance with the disclosed subject matter having an expandable pressure chamber. The pressure chamber 450 is constructed so as to expand as it is pressurized, yet maintain adequate hoop strength at the distal end section to retain the constrained stent. In this embodiment, outer tubular member 120 is constructed of a suitable material or composite of materials to allow the outer tubular member 120 to expand as the pressure chamber is pressurized. Additionally, proximal and distal seals, 720 and 730, respectively, are also formed of an expandable material or composite of materials to increase accordingly to match the dimensions of the outer tubular member. That is, the seals 720 and 730 expand with the outer tubular member to maintain an adequate seal. As the pressure chamber expands, the exposed surface areas of the end seals also increase, resulting in a proportional increase in retraction force at a given fluid pressure. Thus, an expanding pressure chamber provides for greater retraction force at a given pressure. FIG. 12A depicts a cross-sectional view of the distal end of a catheter with an expandable pressure chamber 450 prior to being pressurized. FIG. 12B depicts the same catheter after pressurization. As shown, outer tubular member 120 and the proximal and distal seals 720 and 730 expand under pressure.

The outer tubular member 120 in such an embodiment can be formed of any suitable material or composite that allow expansion. Solely for example, the outer tubular member 120 can be a multilayer tube or balloon-like structure including a flexible layer and a layer having a brittle structure configured to fracture upon expansion. The rigid layer can constrain the medical device during shipping, storage and delivery, but can rupture when pressurized upon expansion of the pressure chamber 450. Once the rigid outer layer is broken, the flexible layer can maintain a seal while significantly increasing in diameter over the pressure chamber. The multilayer outer tubular member can have a brittle outer layer and a flexible inner layer. Additionally or alternatively, the outer tubular member 120 can have a rigid inner layer and a flexible outer layer, wherein the rigid layer is made of a material that is dissolvable by a selected fluid medium. The pressure chamber 450 can be pressurized with the fluid medium, dissolving the rigid structure and thereby allowing the flexible outer layer to expand in diameter. The outer tubular member 120 can also be formed of a suitable shape-memory material configured to expand over the pressure chamber when the chamber is filled with a hot fluid. As another alternative, the outer tubular member can have a bi-stable design that transition from a contracted configuration during delivery to an expanded configuration upon increased fluid pressure in the pressure chamber.

The proximal and distal seals of the expandable chamber configuration can be formed of any suitable materials. Solely for example, the seals can be rubber or silicon. In embodiments having an expandable pressure chamber, the seals can be formed of a low durometer rubber having a compressed condition and an expanded condition. The seals can be significantly compressed and deformed in the initial delivery configuration, transitioning to the expanded condition when the pressure chamber is pressurized. Alternatively, the seals can be made of hydrophilic polymers that absorb fluid in the pressure chamber and expand along with the outer tubular member. Alternatively, the proximal and distal seals can be made of hydrophobic material.

The inner tubular member and outer tubular member each can be a single piece construction, or an assembly of components, and can be made of any suitable material. For example, suitable materials include, but are not limited to polymer materials such as nylon, urethane, polyurethane, PEEK, PTFE, PVDF, Kynar, PE, HDPE, a trilayer material including L25, Plexar, PEBAX, or polyethylene of various suitable densities. Furthermore, at least a portion of the inner and/or outer tubular members can be constructed of an alloy or metallic material, such as stainless steel hypodermic tubing or the like.

As a further alternative, the inner tubular member and/or the outer member each can be constructed of multiple outer tubular members. A stop can further form a joint for two adjacent tubular members. The outer tubular member can further be constructed of a composite comprising a fabrication of several different materials, such as a co-extrusion of different polymers, or a fiber-reinforced composite material such as fiber reinforced resin materials or braided materials. Solely for example, exemplary embodiments can include a braided tube with a PTFE liner, a Polyimide middle layer with braiding and a Pebax 72D outer layer. Additionally, to improve flexibility, helical or spiral member configurations can be used in the construction of the inner and outer tubular members.

Exemplary constructions for the outer tubular member include a single layer of polyimide or PEEK; a trilayer material of L25, Plexar, HDPE; or a braided tube with a PTFE liner, a Polyimide middle layer braiding middle layer, and a Pebax 72D outer layer. The inner and/or outer tubular members can also be reinforced by the addition of a strengthening member, such as, for example, a wire coil. In one embodiment, the inner tubular member is reinforced by the addition of a strengthening member along a length corresponding to the pressure chamber.

It is further contemplated that the inner and outer tubular members can be constructed of other biocompatible material. As such, the inner and outer tubular members of the catheter can be constructed from the above-identified polymers, combinations or blends of these polymers, whether alone or in combination with other materials, or other bioabsorbable materials.

The inner and outer tubular members can be manufactured using a variety of known techniques such as but not limited to: extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes are to be incorporated, various metallic manufacturing techniques can be used, such as but not limited to, machining, tube drawing processes, drilling, milling, EDM, other deformation methods, plating, sputtering, electrografting, sintering, and depositioning e-polishing, among others. In one embodiment of the disclosed subject matter, the inner tubular member includes a stainless steel hypotube at least at its proximal end.

Additionally, the inner and outer tubular members can be constructed from PE, polypropylene, Kynar, or urethane by an extrusion process using an extruder such as that available from any of a number of known suppliers. The materials can be post-processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number of suitable coatings and coating techniques subject to patent matters owned by Abbott Laboratories such as U.S. Pat. No. 6,541,116, U.S. Pat. No. 6,287,285, and U.S. Pat. No. 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel, or lubricious coatings.

The inner and outer tubular members can have any suitable cross-sectional shape, including elliptical, polygon, or prismatic, although a circular cross-section generally is preferred. The inner and outer tubular members can also have any suitable size and diameter depending upon the desired application. The catheter is suitably sized and configured for delivery within a corresponding body lumen for the intended indication, such as a vasculature for vascular intervention.

As previously noted, the outer tubular member can include an outer layer and an inner layer. The outer tubular member can be provided with an inner layer attached to or formed with an outer layer. The inner layer or liner can include a lubricious material to facilitate the sliding of the outer tubular member in a proximal direction when the outer tubular member is retracted. For example, different types of polymers such as PTFE or high-density polyethylene (HDPE) can be used for the inner layer. Additionally, other lubricious polymers can be used. The outer layer, as embodied herein, provides sufficient strength to capture a medical device therein, as well as allow movement between the first position and the second position. The multiple layers can be formed separately and adhered or bonded together or co-extruded as a single member.

In further accordance with the disclosed subject matter the outer tubular member can include a reinforcing layer disposed between the outer layer and the inner layer, such as a braided material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

When the outer tubular member is provided with an inner layer, outer layer and a reinforcing layer, the outer tubular member can be formed in the following manner. First, inner layer is formed through a tubular extrusion process, and disposed about a forming mandrel (not shown). The forming mandrel, as embodied herein, has a shape that corresponds to the desired shape of the inside of the outer tubular member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over reinforcing layer. Each portion of outer layer can be a different material selected to provide a different durometer as described above. The two portions of outer layer can overlap by an amount such as approximately 0.1 inches. Next, a sleeve of heat shrinkable material is positioned over the entire outer tubular member assembly. Finally, heat is applied to the assembly. When heat is applied, the heat shrinkable tubing shrinks, and causes inner layer to fuse with outer layer, trapping reinforcing layer therebetween. The heating process also causes inner layer to conform to the shape of the forming mandrel. After the assembly cools, the heat shrinkable tubing is cut away, leaving behind the outer tubular member.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a stent throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A catheter comprising:
    an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member;
    an outer tubular member movable relative to the inner tubular member, the outer tubular member having a proximal end, a distal end and an interior surface directed toward the exterior surface of the inner tubular member;
    a proximal seal extending from the interior surface of the outer tubular member toward the exterior surface of the inner tubular member, the proximal seal located proximal to the fluid flow port;
    a distal seal extending from the exterior surface of the inner tubular member toward the interior surface of the outer tubular member, the distal seal located distal to the fluid flow port;
    a pressure chamber defined by the proximal seal, the distal seal, the exterior surface of the inner tubular member and interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction; and
    a spring disposed to bias the outer tubular member in the proximal direction.

2. The catheter of claim 1, wherein the inner tubular member further includes a guidewire lumen defined therein.

3. The catheter of claim 2, wherein the guidewire lumen is defined by guidewire tube disposed within the fluid lumen.

4. The catheter of claim 1, further comprising a marker secured to the inner tubular member to seal a distal end of the fluid lumen distal of the fluid flow port.

5. The catheter of claim 1, wherein the fluid lumen is configured to receive a guidewire, the fluid lumen further comprising proximal and distal guidewire seals to seal around a guidewire disposed therethrough.

6. The catheter of claim 1, wherein the proximal seal and the distal seal are formed of at least one of hydrophilic material and hydrophobic material.

7. The catheter of claim 1, further comprising a bellows component attached to the exterior surface of the inner tubular member and in fluid communication with the fluid flow port, wherein fluid introduced through fluid flow port expands the bellows component to retract the outer tubular member.

8. The catheter of claim 1, wherein the spring is formed of metal or metal alloy.

9. The catheter of claim 1, wherein the spring has a constant pitch.

10. The catheter of claim 1, wherein the spring has a constant diameter.

11. The catheter of claim 1, further comprising a dissolvable adhesive to maintain the spring in a compressed configuration until the adhesive is dissolved.

12. The catheter of claim 1, further comprising:
a releasable clip attached to the spring to temporarily secure the spring in a compressed configuration.

13. The catheter of claim 12, further comprising a pullwire coupled to the releasable clip to deploy the clip and release the spring.

14. The catheter of claim 1, further comprising:
an inflatable balloon disposed to retain the spring in a compressed configuration when the inflatable balloon is inflated.

15. The catheter of claim 14, wherein the balloon has an interior chamber and a balloon port defined therein, the balloon being moveable to align the balloon port with the fluid flow port for fluid communication with the chamber of the balloon.

16. The catheter of claim 1, wherein the proximal seal and the distal seal are expandable.

17. The catheter of claim 1, wherein the proximal and distal seals are made of low durometer rubber having a compressed condition and an expanded condition.

18. The catheter of claim 1, wherein the outer tubular member is radially expandable upon increased fluid pressure in the pressure chamber.

19. The catheter of claim 1, wherein the outer tubular member comprises a multilayer tube having a flexible inner layer and a rigid outer layer.

20. The catheter of claim 1, wherein the outer tubular member comprises a multilayer tube having a rigid inner layer and a flexible outer layer, the rigid inner layer being formed of a dissolvable material.

21. The catheter of claim 1, wherein the outer tubular member is formed of a shape memory material, the outer tubular member being radially expandable upon increased fluid temperature in the pressure chamber.

22. The catheter of claim 1, wherein the outer tubular member is formed of a bi-stable material having a contracted configuration and an expanded configuration; the outer tubular member transitioning from the contracted configuration to the expanded configuration upon increased fluid pressure in the pressure chamber.

23. The catheter of claim 1, further comprising a strengthening member disposed in the inner tubular member along a length corresponding to the pressure chamber.

24. The catheter of claim 1, further comprising a stent seat disposed at the distal end of the inner tubular member; and a stent disposed about the stent seat.

25. The catheter of claim 1, wherein the pressure chamber maintains structural integrity up to a positive pressure of approximately 750 psi.

26. The catheter of claim 25, wherein the pressure chamber maintains structural integrity up to a negative pressure of approximately 14 psi.

* * * * *